United States Patent
Piatesi et al.

(10) Patent No.: US 9,834,798 B2
(45) Date of Patent: Dec. 5, 2017

(54) PROCESS FOR PREPARING SEBACIC ACID

(71) Applicant: BASF SE, Ludwigshafen (DE)

(72) Inventors: Andrea Piatesi, Mannheim (DE); Kai-Uwe Baldenius, Heidelberg (DE); Klaus Ditrich, Goennheim (DE); Alois Kindler, Gruenstadt (DE); Marta Zajaczkowski-Fischer, Neuhofen (DE); Ralf Boehling, Lorsch (DE); Alwin Rehfinger, Mutterstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/423,448

(22) PCT Filed: Sep. 3, 2013

(86) PCT No.: PCT/EP2013/068144
§ 371 (c)(1),
(2) Date: Feb. 24, 2015

(87) PCT Pub. No.: WO2014/037328
PCT Pub. Date: Mar. 13, 2014

(65) Prior Publication Data
US 2015/0259713 A1    Sep. 17, 2015

(30) Foreign Application Priority Data
Sep. 7, 2012 (EP) ................................ 12183534

(51) Int. Cl.
| | | |
|---|---|---|
| C12P 7/64 | (2006.01) | |
| C12N 9/88 | (2006.01) | |
| C07H 21/04 | (2006.01) | |
| C07K 1/00 | (2006.01) | |
| C07C 51/235 | (2006.01) | |
| C07C 51/373 | (2006.01) | |

(52) U.S. Cl.
CPC .......... C12P 7/6427 (2013.01); C07C 51/235 (2013.01); C07C 51/373 (2013.01); C12P 7/6409 (2013.01); C12Y 402/01053 (2013.01)

(58) Field of Classification Search
CPC ........... C12Y 402/01053; C12P 7/6409; C12P 7/6427; C07C 51/235; C07C 51/373; C07C 59/147; C07C 55/20; Y02P 20/52
USPC .................. 435/134, 232; 536/23.2; 530/350
See application file for complete search history.

(56) References Cited

U.S. PATENT DOCUMENTS

| | | | |
|---|---|---|---|
| 4,582,804 A | | 4/1986 | Litchfield et al. |
| 5,952,517 A | * | 9/1999 | Ries ........................ C07C 45/27 554/132 |
| 5,965,771 A | * | 10/1999 | King ........................ C07C 51/47 562/580 |
| 2010/0203600 A1 | | 8/2010 | Dubois |

FOREIGN PATENT DOCUMENTS

| | | |
|---|---|---|
| JP | S4919085 A | 2/1974 |
| WO | WO-2008/119735 A1 | 10/2008 |

OTHER PUBLICATIONS

Azcan et al., Obtaining 2-octanol, 2-octanone, and sebacic acid from castor oil by microwave-induced alkali fusion. Ind. Eng. Chem. Res., 2008, vol. 47: 1774-1778.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Joo et al., Productin of 10-hydroxystearic acid from oleic acid by whole cells of recombinant Escherichia coli containing oleate hydratase from Stenotrophomonas maltophilia. J. Biotechnol., 2012, vol. 158: 17-23.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
BRENDA Information on EC 4.2.1.53-Oleate hydratase; one page downloaded from http://www.brenda-enzymes.org/ on Aug. 4, 2016.*
Guo et al., Protein tolerance to random amino acid change. PNAS., 2004, vol. 101 (25): 9205-9210.*
Khersonsky et al., Enzyme promiscuity: A mechanistic and evolutionary perspective. Annu. Rev. Biochem., 2010, vol. 79: 471-505.*
Todd et al., Plasticity of enzyme active sites. TRENDS in Biochem., Sci., 2002, vol. 27 (8): 419-426.*
Bevers, L., et al., "Oleate Hydratase Catalyzes the Hydration of a Nonactivated Carbon-Carbon Bond," *Journal of Bacteriology* 191 (2009), pp. 5010-5012.
Das, G, et al., "Heptaldehyde and Undecylenic Acid from Castor Oil," *Journal of the American Oil Chemists' Society* 66, No. 7 (1989), pp. 938-941.
Database WPI Week 197423 Thomson Scientific, London, GB; AN 1974-42600V XP002690865, & JP 49 019085 A (Asahi Electrochemical Co Ltd) Feb. 20, 1974 (Feb. 20, 1974).

(Continued)

*Primary Examiner* — Ganapathirama Raghu
(74) *Attorney, Agent, or Firm* — Marshall, Gerstein & Borun LLP

(57) ABSTRACT

A process for preparing sebacic acid by reacting in a first step (i) linoleic acid with water catalyzed by an oleate hydratase to form 10-hydroxy-12-octadecenoic acid, in a second step (ii) pyrolysing the 10-hydroxy-12-octadecenoic acid to 1-octene and 10-oxo-decanoic acid and in a third step (iii) oxidizing the 10-oxo-decanoic acid to sebacic acid.

12 Claims, 3 Drawing Sheets

(56) References Cited

OTHER PUBLICATIONS

Demir, A, et al., "Chemoenzymatic Conversion of Linoleic Acid Into Conjugated Linoleic Acid," *Journal of Agricultural and Food Chemistry* 58, No. (2010), pp. 1646-1652.

Hou, C. T., "Microbial Oxidation of Unsaturated Fatty Acids," *Advances in Applied Microbiology* 41 (1995), pp. 1-23.

Hou, C., "Conversion of Linoleic Acid to 10-Hydroxy-12(Z)-Octadecenoic Acid by *Flavobacterium* sp. (NRRL B-14859)," *Journal of the American Oil Chemists' Society* 71, No. 9 (1994), pp. 975-978.

Hou, C., "Production of Hydroxy Fatty Acids From Unsaturated Fatty Acids by *Flavobacterium* sp. DS5 Hydratase, a C-10 Positional-Andcis Unsaturation-Specific Enzyme," *Journal of the American Oil Chemists' Society* 72, No. 11 (1995), pp. 265-1270.

Hudson, J., et al., "Hydration of Linoleic Acid by Bacteria Isolated from Ruminants," FEMS *Microbiology Letters* 169, No. 2 (1998), pp. 277-282.

Joo, Y. C., et al., "Production of 10-Hydroxystearic Acid from Oleic Acid by Whole Cells of Recombinant *Escherichia coli* Containing Oleate Hydratase from Stenotrophomonas Maltophilia," *Journal of Biotechnology* 158, No. 1 (2012), pp. 17-23.

Kim, Bi-Na, , et al., "Conversion of Oleic Acid to 10-Hydroxystearic Acid by Whole Cells of Stenotrophomonas Nitritireducens," *Biotechnology Letters* 33, No. 5 (2011), pp. 993-997.

Kishimoto, et al., "Two Distinct Pathways for the Formation of Hydroxy FA from Linoleic Acid by Lactic Acid Bacteria," *Lipids* 38, No. 12 (2003), pp. 1269-1274.

"RecName: Full=Oleate hydratase; EC=4.2.1.53; AltName: Full=Fatty acid double bond hydratase; AltName: Full=Fatty acid hydratase" (Sep. 22, 2009), retrieved from Bioinformatics Institute (EBI) accession No. UNIPROT: C7DLJ6, Database accession No. C7DLJ6 sequence.

Schroepfer, G., et al., Enzymatic Conversion of Linoleic Acid to 10D-hydroxy-Δ12-cis-Octadecenoic Acid, *Journal of Biological Chemistry* 245, No. 15 (1970), pp. 3798-3801.

Spencer, H., et al, "Asymmetric Induction in the Pyrolysis of .Beta.-Hydroxyolefins," *The Journal of Organic Chemistry* 41, No. 14 (1976), pp. 2485-2487.

International Search Report for International Application No. PCT/EP2013/068144, dated Jan. 8, 2014.

* cited by examiner

A

B

A

B

PROCESS FOR PREPARING SEBACIC ACID

CROSS-REFERENCE TO RELATED APPLICATIONS

This is the U.S. national phase of International Application No. PCT/EP2013/068144, filed Sep. 3, 2013, which claims the benefit of European Patent Application No. 12183534.2, filed Sep. 7, 2012.

The present invention relates to a novel process for preparing sebacic acid. In particular, this invention relates to the chemo-enzymatic production of sebacic acid starting from linoleic acid which is hydroxylated to 10-hydroxy-12-octadecenoic acid and further transformed to sebacic acid.

STATE OF THE ART

Sebacic acid is currently produced from castor oil by alkaline cleavage of ricinoleic acid (12-hydroxy-9-cis-octadecenoic acid) under pressure and high temperatures.

Sebacic acid and its derivatives are important components in biodegradable polymers, plasticizers, lubricants, hydraulic fluids, candles and cosmetics.

An overview on the microbial oxidation of unsaturated fatty acids is described in following publication: Hou C. T. (1995) Adv. Appl. Microbiol., 41, 1-23.

The enzymatic hydration of linoleic acid to 10-hydroxy-12-octadecenoic acid by a *pseudomonas* preparation is described with a 57% yield by Schroepfer G. J. et al. (1970) J. Biol. Chem., 245, 3798-3801).

In U.S. Pat. No. 4,582,804 Litchfield & Pierce disclose that cells of *Rhodococcus rhodochrous* catalyze the hydration of linoleic acid to 10-hydroxy-12-octadecenoic acid with a 22% yield.

Hou reported the hydration of linoleic acid to 10-hydroxy-12-octadecenoic acid by the *Flavobacterium* DS5 enzyme system with a 55% yield (Hou C. T. (1994) J. Am. Oil Chem. Soc., 71, 975-978).

The same conversion has also been shown using strains of *Enterococcus faecalis* from the ovin rumen with a 22% yield (Hudson J. A. et al. (1998) FEMS Microbiology Letters, 169, 277-282).

A report by Demir et al. describes the chemoenzymatic conversion of linoleic acid to cis-9,trans-11-octadecadienoic acid (CLA), a compound having anticancer, fat-reducing and hypertension-suppressing properties. Linoleic acid was converted to 10-hydroxy-12-octadecenoic acid by *Lactobacillus plantarum*, followed by a treatment with iodine under microwave irradiation to produce CLA in high yield (Demir A. S. et al. (2010) J. Agric. Food Chem., 58, 1646-1652).

Although many reports have been describing the use of whole microorganisms or cell extracts for the hydration of unsaturated fatty acids, no enzyme has been characterized in detail until 2009. Bevers et al. first described the isolation, recombinant expression in *E. coli* and characterization of the oleate hydratase (EC 4.2.1.53) from *Elizabethkingia meningoseptica* (Bevers L. E. et al. (2009) J. Bacteriol., 191, 5010-5012).

A method for the production of hydroxy fatty acids by using a hydratase from *Streptococcus pyogenes* was described in WO 2008/119735.

Recent reports showed that a oleate hydratase from *Stenotrophomonas maltophilia* and from *Lysinibacillus fusiformis* are able to hydrate linoleic acid, although with reduced specific activity compared to oleic acid (Young-Chul Joo et al. (2012) J. Biotechnol., 158, 17-23 and Bi-Na Kim et al. (2011) Appl. Microbiol. Biotechnol., online)

Objective

Due to the increasing demand of sebacic acid it is therefore an object of the present invention to provide a novel route to the synthesis of sebacic acid starting from educts other than ricinoleic acid which are easily accessible.

SUBJECT MATTER OF THE INVENTION

Figure 1:
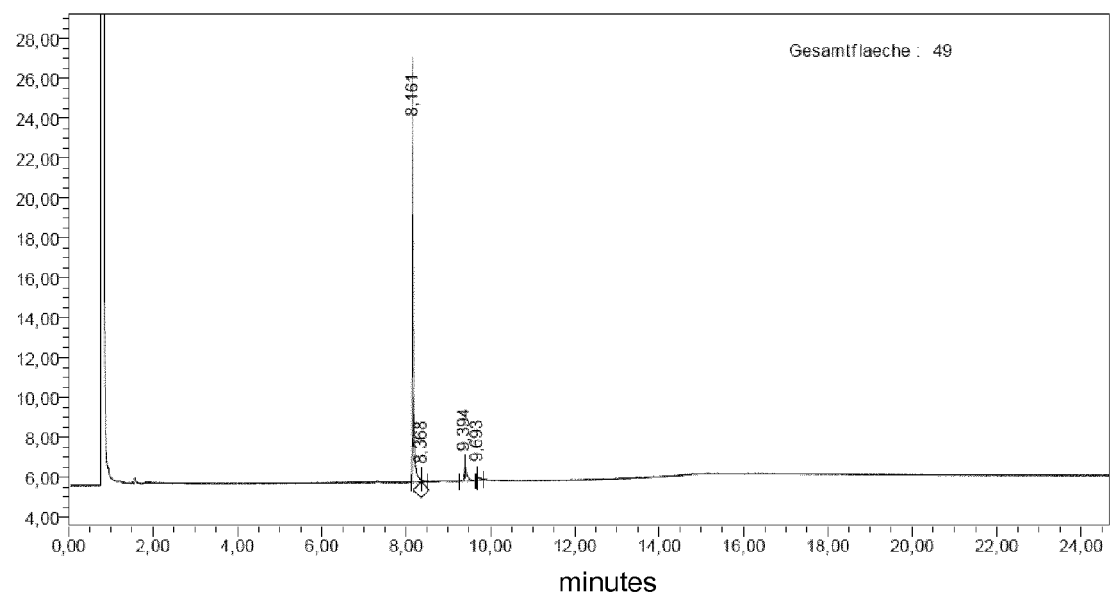
FIG. 1A shows oleic acid incubated o/n at RT with *E. coli* TOP10 only. Retention time of oleic acid: 8.161 min.
FIG. 1B shows oleic acid incubated o/n at RT with *E. coli* TOP10 expressing oleate hydratase. Retention time of 10-HSA: 9.340 min.
Figure 1:
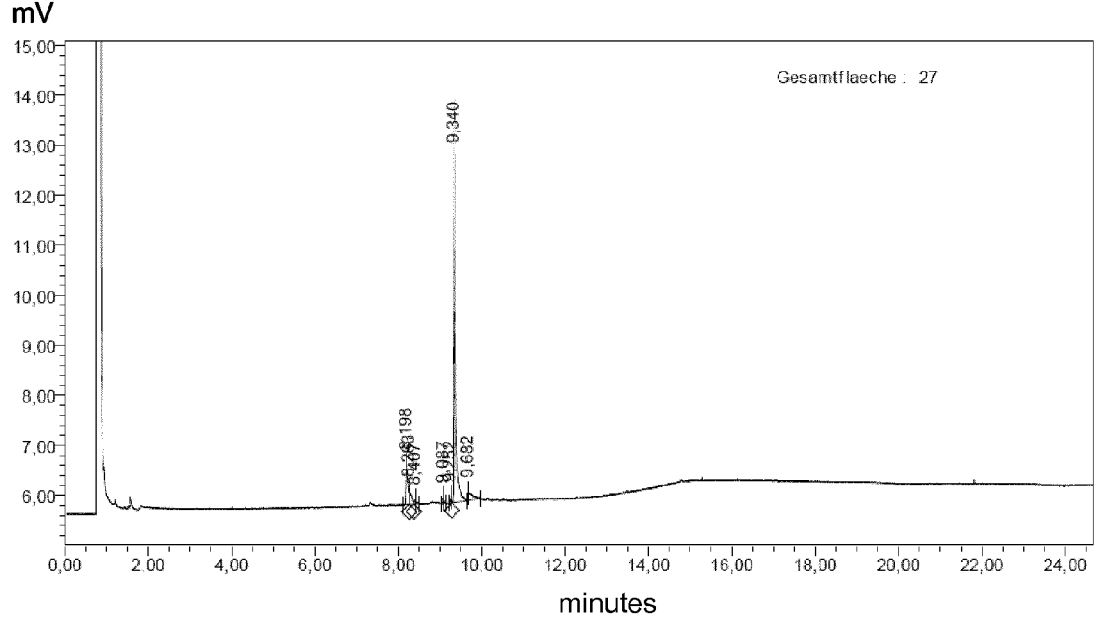

The object is achieved in accordance with the claims by a process for preparing sebacic acid by reacting in a first step (i) linoleic acid with water catalyzed by an oleate-hydratase to form 10-hydroxy-12-octadecenoic acid, in a second step (ii) pyrolysing the 10-hydroxy-12-octadecenoic acid to 1-octene and 10-oxo-decanoic acid and in a third step (iii) oxidizing the 10-oxo-decanoic acid to sebacic acid.

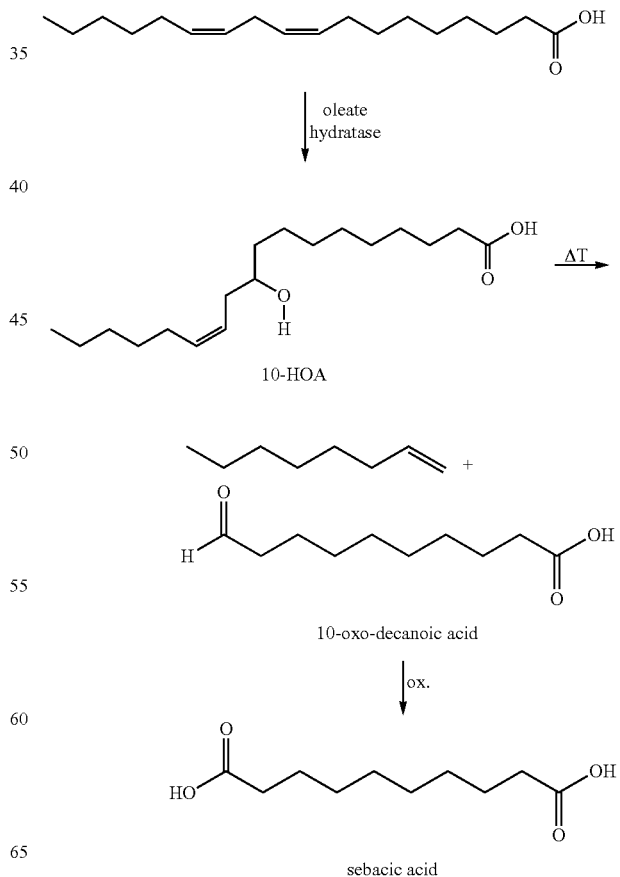

Step (i)

The process according to the invention starts with the conversion of linoleic acid to 10-hydroxy-12-octadecenoic acid. For step (i) of the inventive process chemically pure linoleic acid can be used as well as substrates which contain linoleic acid as a main component, preferably more than 60%, more preferred more than 70% or 80% by weight of the substrate.

Such substrates can be prepared from oil having a high linoleic acid content in form of glycerol esters by hydrolyzing the glycerol ester and recovering the linoleic acid in form of the free acid or its salts. Such oils are for example safflower oil (78% linoleic acid), grape seed oil (73% linoleic acid), poppy seed oil (70% linoleic acid) or mostly preferred sunflower oil (68% linoleic acid).

If linoleic acid is produced from a complex oil such as sunflower oil, the fatty acid preparation may contain in addition to linoleic acid other fatty acids which can be present when performing step (i) of the inventive reaction. These other fatty acids can be eliminated from the reaction at later reaction steps, preferably after step (ii).

As enzymes suitable for step (i) there are numerous oleate-hydratases in the prior art as described above e.g. from the organisms *Pseudomonas, Rhodoccocus, Flavobacterium, Enterococcus, Lysinibacillus, Lactobacillus, Stenotrophomonas, Elizabethkingia*.

These enzymes are known in the art to convert linoleic acid to 10-hydroxy-12-octadecenoic acid. In addition to those enzymes other oleate-hydratases can be easily found by the skilled person by screening microorganisms using as a model reaction the conversion of oleic acid to 10-hydroxystearic acid or the targeted reaction linoleic acid to 10-hydroxy-12-octadecenoic acid. This reaction can be performed in test tube assays and so simultaneously thousands of microorganisms can be screened in short time.

As the sequence of some oleate-hydratases is known it is also possible to screen in silico genomes of microorganisms for other oleate-hydratases and test the positive populations for the conversion of oleic acid to 10-hydroxystearic acid or the targeted reaction linoleic acid to 10-hydroxy-12-octadecenoic acid.

Another way is the genetic engineering of known oleate hydratases in order come to enzymes with improved activity or better temperature or solvent resistance by comparing the sequences from known oleate hydratases in order to detect conserved or homologous regions and to find starting points for a directed gene mutagenesis.

A preferred enzyme is the oleate hydratase according to EC 4.2.1.53. A representative of this class of enzymes is the enzyme from *Elizabethkingia miningoseptica* (Bevers et al (2009) J. Bacteriol. 191, 5010-5012). The nucleotide sequence and the corresponding amino acid sequence are disclosed as SEQ ID NO:1 and 2.

A preferred enzyme is one having SEQ ID NO: 2, or a fragment of said polypeptide sequence, wherein said fragment is sufficient for a protein having the enzymatic activity of an oleate hydratase, or nucleic acid sequences comprising a nucleotide sequence which codes for an oleate hydratase and which hybridizes to a complementary strand of the nucleotide sequence coding for SEQ ID NO:2 under stringent conditions, or comprising a fragment of said nucleotide sequence, wherein the fragment is sufficient to code for a protein having the enzymatic activity of an oleate-hydratase.

The invention further relates to an enzyme having the enzymatic activity of an oleate-hydratase and the amino acid sequence depicted in SEQ ID NO: 2 or an amino acid sequence which is at least 75% or 80%, preferably at least 85%, 90% or 95%, more preferably at least 95% or 97% and most preferably at least 98% or 99% identical to the amino acid sequence depicted in SEQ ID NO:2.

To improve enzyme solubility and expression level, such enzymes can be recombinantely expressed with N- (or C)-terminal fusion partners (protein or peptide). Typical proteins or tags used as fusion partners for improved solubility and/or expression levels are: maltose binding protein, thioredoxin, green fluorescence protein, glutathione-S-transferase, disulfide oxidoreductase/isomerase, T7 tag, SET tag, Nus A, Mistic and SUMO.

In the context of this invention the term "hybridization under stringent conditions" means that the hybridization is performed in vitro under conditions stringent enough to ensure a specific hybridization. Stringent in vitro hybridization conditions are known to the person skilled in the art, and can be found in the literature (e.g. Sambrook and Rus-sell (2001) Molecular Cloning: A Laboratory Manual, 3rd edition, Cold Spring Har-bour Laboratory Press, Cold Spring Harbour, N.Y.). The term "specific hybridization" refers to the fact that a molecule preferably binds to a certain nucleic acid sequence, the target sequence, under stringent conditions, if the target sequence is part of a complex mixture of, for example, DNA or RNA molecules, but does not bind, or at least to a considerably lesser degree, to other sequences.

Stringent conditions depend on the circumstances. Longer sequences hybridize specifically at higher temperatures. In general, stringent conditions are selected so that the hybridization temperature is approximately 5° C. below the melting point (Tm) for the specific sequence at a defined ionic strength and a defined pH value. Tm is the temperature (at a defined pH value, a defined ionic strength and a defined nucleic acid concentration) at which 50% of the molecules complementary to the target sequence hybridize to the target sequence in the equilibrium state. Typically, stringent conditions are those in which the salt concentration is at least about 0.01 to 1.0 M of sodium ion concentration (or the concentration of another salt) at a pH of between 7.0 and 8.3 and the temperature is at least 30° C. for short molecules (i.e. for example 10 to 50 nucleotides). Furthermore, stringent conditions can comprise the addition of agents, such as formamide, which destabilize the hybrids. In hybridization under stringent conditions as used herein, nucleotide sequences which are at least 60% homologous to each other usually remain hybridized to each other. Preferably, the stringent conditions are selected in such a way that sequences which are homologous to each other by at least about 65%, prefer-ably at least about 70%, and especially preferably at least about 75%, or more, usually remain hybridized to each other. A preferred, non-limiting example for stringent hybridization conditions are hybridizations in 6× sodium chloride/sodium citrate (SSC) at about 45° C., followed by one or more washing steps in 0.2×SSC, 0.1% SDS at 50 to 65° C. The temperature ranges, for example, under standard hybridization conditions depending on the type of nucleic acid, between 42° C. and 58° C. in an aqueous buffer at a concentration of 0.1 to 5×SSC (pH 7.2).

If an organic solvent, e.g. 50% formamide, is present in the above-mentioned buffer, the temperature under standard conditions is about 42° C. Preferably, the hybridization conditions for DNA:DNA hybrids are for example 0.1×SSC and 20° C. to 45° C., preferably 30° C. to 45° C. Preferably, the hybridization conditions for DNA:RNA hybrids are for example 0.1×SSC and 30° C. to 55° C., preferably between 45° C. to 55° C. The hybridization temperatures mentioned above are determined for example for a nucleic acid having a length of about 100 base pairs and a G/C content of 50% in the absence of formamide. The person skilled in the art knows how the required hybridization conditions can be determined using the above mentioned, or the following, textbooks: Current Protocols in Molecular Biology, John Wiley & Sons, N. Y. (1989), Hames and Higgins (publisher) 1985, Nucleic Acids Hybridization: A Practical Approach, IRL Press at Oxford University Press, Oxford; Brown (publisher) 1991, Essential Molecular Biology: A Practical Approach, IRL Press at Oxford University Press, Oxford.

The stereospecificity of the enzymatic hydration is not critical for the inventive process. Consequently either the 10(R) or the 10(S)-hydroxy-12-octadecenoic acid or mixtures (racemates) produced in step (i) can be used in the following step (ii).

Enzymatic conversion of linoleic acid to 10-hydroxy-12-octadecenoic acid can be performed in a reaction medium which contains the linoleic acid and water. If the linoleic acid is used in form of the free acid (the oil phase) the water or a buffered water containing solution with the enzyme forms a second liquid phase (the water phase). The two liquid phase should be mixed thoroughly in order to form an emulsion for a quick reaction.

However, step (ii) can also be performed with immobilized enzymes, which can easily be removed from the reaction medium and be recycled. Enzymes can be generally immobilized by different methods such as adsorption, covalent binding, membrane encapsulation, gel encapsulation and cross-linking. The properties of the carrier material for immobilization shall be optimized in order to avoid enzyme inactivation. Typical carriers can be either organic (natural and non-natural) or inorganic materials. Inorganic materials usually have good tolerance against pressure, while organic materials show good chemical stability. Inorganic carriers are typically porous materials based on silicon- or aluminum oxides, or mixtures thereof. Natural organic carriers are for example polysaccharides like cellulose, starch, dextran, agar or chitin. Proteins like collagen, gelatin or albumin can also be used. Synthetic organic carriers include poly(meth)acrylates, polyacrylamide, vinyl- and allylpolymers, polyesters, polyamides.

Step (i) can be performed in a 2-phase system, where the enzyme preparation (aqueous phase) is added to the organic phase containing linoleic acid. The ratio aqueous phase/linoleic acid phase can be varied in a broad range.

The reaction can be performed with or without additional solvents. With regard to the selection of the solvent, the person skilled in the art is guided by the product yield, reaction rate, manageability of the suspensions formed and the cost of the solvent.

Advantageous solvents are those which can be mixed with the linoleic acid, are chemically inert, i.e. do not react with the enzyme or inhibit the enzymatic activity.

Typical organic solvents in biocatalytic processes are: hexane, heptane, dodecane, hexadecane, ethyl ether, isopropyl ether, butyl ether, tetrahydrofuran, dioxane, toluene, dimethyl sulfoxide, acetone, 2-pentanone, 2-heptanone. The reaction temperature for step (i) depends from the thermal stability of the enzyme used and is usually between 10 and 50° C., preferred between 20 and 40° C. However, if an enzyme with a high thermal stability is used also reaction temperatures of above 50° C. are possible.

The formed 10-hydroxy-12-octadecenoic acid can be recovered from reaction medium by conventional processes such as crystallization or extraction.

For the next step of the inventive reaction, i.e. step (ii), the 10-hydroxy-12-octadecenoic acid can be used in the form of the free acid or in the form of an ester, preferred a lower alkyl ester such as methyl or ethyl ester of 10-hydroxy-12-octadecenoic acid.

If an ester of 10-hydroxy-12-octadecenoic acid shall be used in the reaction, the 10-hydroxy-12-octadecenoic acid recovered from step (i) can be esterified by chemical or enzymatic methods before the pyrolysis of step (ii). A preferred way for esterification is the enzymatic conversion by a lipase.

Step (ii)

For the description of this step (ii) the term "10-hydroxy-12-octadecenoic acid" shall mean either the free acid 10-hydroxy-12-octadecenoic acid or an ester of 10-hydroxy-12-octadecenoic acid, for example a methyl or ethyl ester of 10-hydroxy-12-octadecenoic acid.

The pyrolysis of 10-hydroxy-12-octadecenoic acid to 10-oxo-decanoic acid is a retro-ene-type reaction. In order to select for the retro-ene rearrangement and to suppress the competing dehydration reaction it is best to have a fast vaporization of the 10-hydroxy-12-octadecenoic acid.

The reaction can be performed at temperatures from above 400 up to 800° C., preferred from 500 to 600° C. The optimum temperature range depends on the residence time of the substrate as well as on the nature of the substrate. If a methyl ester of 10-hydroxy-12-octadecenoic acid is used the best results have been achieved with temperatures of 600° C. and a residence time of 1-2 seconds in a microreactor. If the free acid 10-hydroxy-12-octadecenoic acid is used instead of the ester a complete conversion of the 10-hydroxy-12-octadecenoic acid could be detected lower temperatures such as 575° C. However, the selectivity for the retro-ene reaction over the dehydration is less with the free acid 10-hydroxy-12-octadecenoic acid than with the methylester of 10-hydroxy-12-octadecenoic acid. For details compare the working examples.

The reaction can be performed in a milli- or microreactor, e.g. a capillary with a diameter of 0.1 to 3 mm. Crucial aspects are a high heating rate and a fast vaporization in a milli- or microevaporator with residence times of <10 seconds, preferably <1 second. In order to maintain these characteristics, milli- or microstructured apparatus known to those skilled in the art are suitable. The reaction can be performed with or without a solvent. If a solvent is used the solvent can be added in up to 99% (w/w). The solvent used should not react or decompose at the temperatures and conditions used during the pyrolysis. A preferred solvent is chosen from the group of stable ethers, such as THF or dioxane. THF is the most preferred solvent for step (ii).

Water can also be added to the reaction mixture.

The 10-oxo-decanoic acid formed in step (ii) can be dependent on the starting material 10-hydroxy-12-octadecenoic acid either the free acid 10-oxo-decanoic acid or the corresponding ester of 10-oxo-decanoic acid. For the description of this step (ii) the term "10-oxo-decanoic acid" shall mean the free acid as well as the ester of 10-oxo-decanoic acid.

The 10-oxo-decanoic acid can be separated from the second product of the retro-ene rearrangement (1-octene) by conventional methods such as distillation or extraction. In the case of a non pure linoleic acid as starting material, f.ex. sunflower oil hydrolysates, the non-transformed fatty acids (f.ex. stearic acid or 10-hydroxostearic acid) can be removed by conventional methods such as distillation, crystallisaion or extraction.

For the next step, the oxidation of 10-oxo-decanoic acid to sebacic acid, the product mixture of step (ii), consisting of 10-oxo-decanoic acid, 1-octene and possibly other fatty acids, can in general be taken without in between purification or the 10-oxo-decanoic acid can be purified by the above mentioned methods. Both, the methyl ester or the free fatty acid can be used.

Step (iii)

For step (iii) the recovered 10-oxo-decanoic acid can be used in the form of the free acid or the ester.

The oxidation of the aldehyde function in 10-oxo-decanoic acid to the dicarbonic acid sebacic acid can be performed according to well-known procedures, as for example in the oxidation of oxo-aldehydes to oxo carbonic acids, by using mild oxidizing agents like oxygen or air at up to 100° C. and up to 7 bar, either without catalyst or homogenously catalyzed by redox active metals as for example Cu, Fe, Co, Mn, etc. (Industrial Organic Chemistry, Wiley-VCH, H.-J. Arpe (publisher), 2007, pp. 149).

Depending on the purity of the starting material used as linoleic acid source in step (i) and depending on the application of the sebacic acid it could be necessary to have additional purification and recovery steps in the process according to the invention which are well known per se for the person skilled in the art. When using the ester of 10-oxo-decanoic acid in step (iii), hydrolysis of the ester will lead to the free sebacic acid.

WORKING EXAMPLES

Example 1

Expression and Characterization of an Oleate Hydratase

The gene encoding the oleate hydratase form Elizabethkingia meningoseptica has been synthesized with a codon usage optimized for E. coli. The following production procedure was adapted from Bevers et al. (Bevers L. E. et al. (2009) J. Bacteriol., 191, 5010-5012).

For recombinant enzyme production, the gene was cloned into the pBAD(HisA) vector (Invitrogen), which allows induction of expression with arabinose. E. coli TOP10 one shot (Invitrogen) was transformed with pBAD(HisA)-OH and plated on LB-Agar-Amp plates (o/n at 37° C.). A single colony was inoculated in 2xYT-Amp and cultured for additional 5 h at 37° C.

Induction of protein expression was achieved by adding 5 mL of this culture to 500 mL 2xYT-Amp supplemented with 0.2% arabinose and by incubation at 37° for additional 18 h. After induction cells were collected by centrifugation (20', 4000 rpm, 4° C.) and resuspended in 20 mM Tris-HCl (pH 8), 50 mM NaCl and 1 mM CaCl2.

The cell suspension was sonicated (3', 15" on/off cycles, 80% amplitude at 4° C.) and the clear supernatant was used in most of the biocatalytic conversions described in this report (typically 40 mg/mL total protein; ≈13% oleate hydratase based on Agilent 2100 Bioanalyzer). The enzyme has also been further purified by Ni-affinity-chromatography (His-tag purification). In this case the induced cells were resuspended in 20 mM Tris-HCl (pH8), 50 mM NaCl, 1 mM CaCl2 and 10 mM imidazole. The washing buffer during purification contained 20 mM imidazole and protein elution was achieved with 500 mM in the same buffer. The fractions containing oleate hydratase were collected and dialyzed against 20 mM Tris-HCl (pH 8), 50 mM NaCl and 1 mM CaCl2. The enzyme stock solution (5.8 mg/mL) was stored at 4° C.

The identity of the of the expressed protein has also been confirmed by a N-terminal protein sequencing.

Example 2

Conversion of Oleic Acid to 10-Hydroxy-Stearic Acid (10-HSA)

As a first step the recombinantely produced oleate hydratase of Example 1 was characterized for its wild-type activity on oleic acid (OA) to produce 10-hydroxystearic acid (10-HSA). Bacteria expressing the oleate hydratase have been sonicated as described in example 1 and 200 µL of the clear supernatant (5 mg/mL total protein content, ≈600 µg oleate hydratase) were added to an emulsion containing 10 mM oleic acid in 20 mM Tris-HCl (pH 8), 50 mM NaCl and 1 mM CaCl2 (final volume 2 mL).

As a negative control, the same reaction was carried out using the supernatant of sonicated E. coli TOP10 not expressing the oleate hydratase (5.6 mg/mL total protein content, no oleate hydratase). The reaction mixture was incubated under stirring o/n at room temperature. The reaction was stopped by adding 50 µL of 3M HCl (final pH 1-2).

At this point 4 mL of MTBE were added to the reaction mixture in order to extract the organic substrate (OA) and product (10-HSA). The reaction products were derivatized by adding 500 µL trimethylsulfoniumhydroxide (TMSH; 0.1 M in methanol) to 100 µL of product solution (30' at 100° C.) and analyzed by GC.

FIG. 1 shows the GC analytics of this enzymatic conversion.

FIG. 1 (A) Oleic acid incubated o/n at RT with E. coli TOP10 only. Retention time of oleic acid: 8.161 min. (B) Oleic acid incubated o/n at RT with E. coli TOP10 expressing oleate hydratase. Retention time of 10-HSA: 9.340 min.

As expected, the oleate hydratase expressed in TOP10 E. coli cells was able to convert oleic acid to 10-HSA almost completely (>95%). The sonicated E. coli TOP10 cells without oleate hydratase did not convert oleic acid.

Example 3

Conversion of Linoleic Acid to 10-Hydroxy-12-Octadecenoic Acid (10-HOA)

The oleate hydratase was expressed in E. coli TOP10 (10 L culture) according to example 1. Cell lysis was accomplished by resuspending the cell pellet in 100 mL of 20 mM Tris-HCl (pH 8), 50 mM NaCl, 1 mM CaCl2 followed by sonication, as previously described. The total protein concentration was 26 mg/mL (13% oleate hydratase).

The supernatant (300-400 mg of oleate hydratase) was added to a solution containing 900 mL of 20 mM Tris-HCl (pH 8), 50 mM NaCl, 1 mM CaCl2 and 14.4 g linoleic acid (≈50 mM). The reaction mixture was stirred at RT for 72 h. Upon completion of the reaction, the pH was adjusted to 1.5 by adding 3M HCl. The product was then extracted with 1 L MTBE and filtered over 100 g of Celite 535. After removal of MTBE by destillation, the reaction product 10-HOA was obtained in high yield (13.6 g, yield: 89%). Samples for GC and GC-MS analytics were prepared by adding 400 µL N-trimethylsilylimidazole (TSIM) to 100 µL of product solution (30' at 100° C.).

Figure 2:
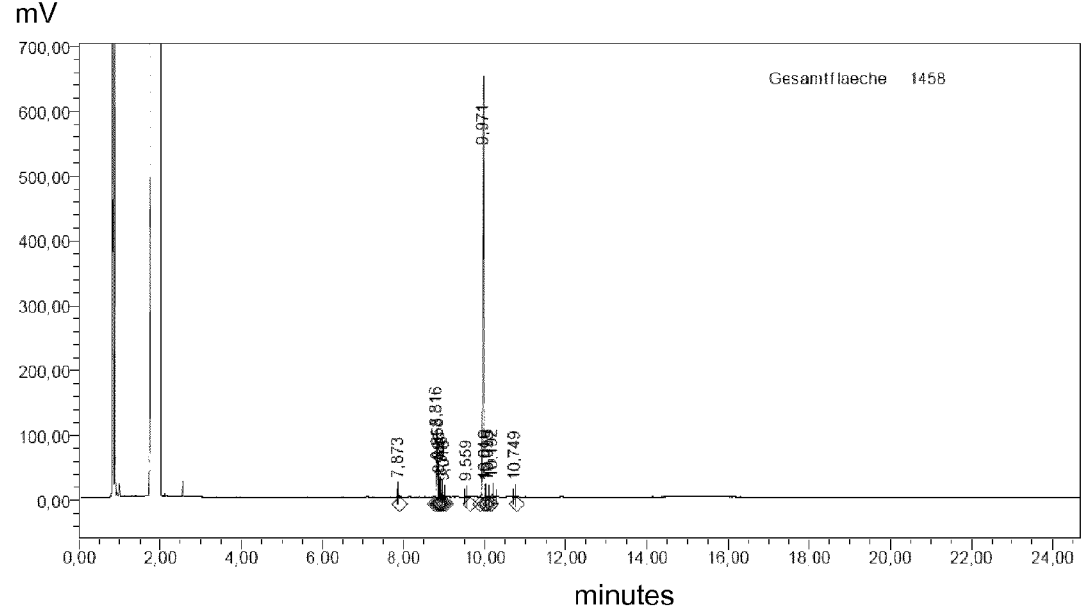
FIG. 2A shows GC analysis of 10-HOA: retention time of 10-110A: 9.971 min.
FIG. 2B shows GC-MS analysis of the reaction product, showing the typical fragmentation pattern for 10-HOA.
Figure 2:
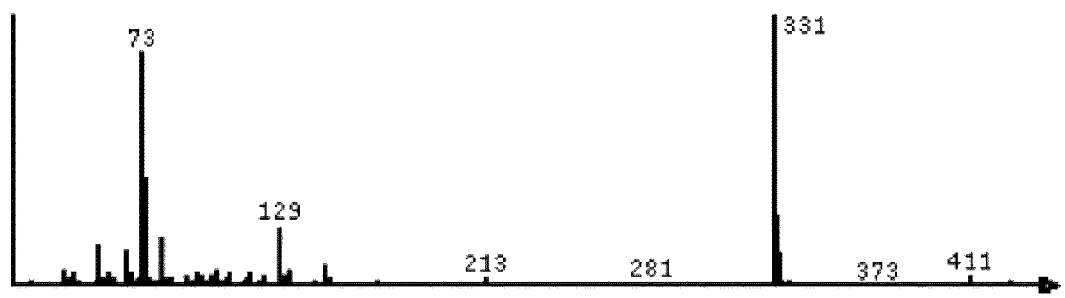
Figure 2:
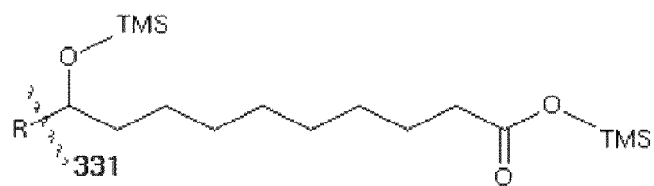

FIG. 2 (A) GC analysis of 10-HOA: retention time of 10-HOA: 9.971 min. (B) GC-MS analysis of the reaction product, showing the typical fragmentation pattern for 10-HOA.

Example 4

Pyrolysis of 10-Hydroxy-12-Octadecenoic Acid (10-HOA) in a Microreactor

Figure 3:
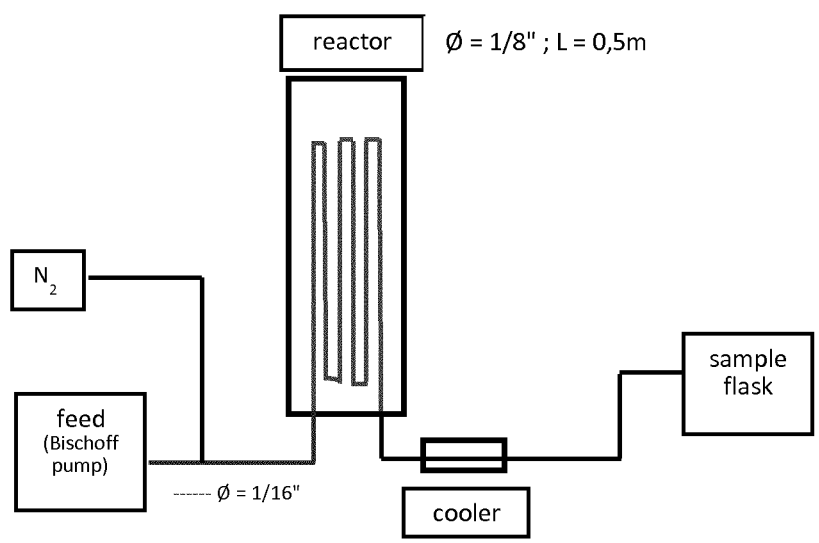
FIG. 3 shows the schematic experimental setup for thermal cleavage of 10-hydroxy-12-octadecenoic acid (10-HOA) in a microreactor.

A microreactor was used for the pyrolysis reactions. The schematic experimental setup is shown in FIG. 3. The feed is dosed into the reactor using a Bischoff HPLC pump. The reactor is a steel tube with an inner diameter of 1/16" immersed in a solid copper block that can be heated up to 800° C. After passing a cooler (aluminium block at room temperature), the product mixture is collected in a flask. With this setup, residence times<1 second are possible. Moreover, the whole mixture is heated up to the desired temperature very fast.

FIG. 3 shows the schematic experimental setup for thermal cleavage of 10-hydroxy-12-octadecenoic acid (10-HOA) in a microreactor.

a. Pyrolysis of 10-HOA methyl ester (Me-10-HOA)

In the first microreactor experiments, the methyl ester of 10-hydroxy-12-octadecenoic acid was chosen as reactant in order to have an easier handling (i.e. better vaporization properties). MTBE and THF were tested as solvents. In the case of MTBE, a large amount of dimethylated 10-oxo-decanoic acid (acetal formation w/methanol) was observed, leading to the conclusion that the solvent is cleaved during the reaction. Therefore, THF was chosen for further experiments (no cleavage products observed). Different temperatures and residence times were evaluated, as well as the effect of water addition (almost equimolar amount of water dissolved in reactant solution). The results are summarized in Table 2.

As seen in Table 2, the temperature has the largest effect on the conversion of 10-hydroxy-12-octadecenoic acid methyl ester, whereas the residence time variation has only a small influence (a greater variation of residence time was not feasible due to the reactor setup but would probably have a larger impact on conversion and selectivity). At 500° C., only around 25% of 10-hydroxy-12-octadecenoic acid methyl ester are converted (entry 1 and 2), at 550° C. it's already around 40% (entries 3-6) and at 600° C. we can have full conversion (entry 7 and 8). Addition of water seems to have a beneficial effect on selectivity. The best results were obtained at 600° C. and a residence time of t=1.3 sec with complete conversion of 10-hydroxy-12-octadecenoic acid methyl ester, around 75% selectivity towards the retro-ene product and only 6.5% selectivity towards the dehydration products (linoleic acid methyl ester and isomers, entry 8).

TABLE 2

Results of 10-hydroxy-12-octadecenoic acid methyl ester pyrolysis in microreactor (analyzed by GC of silylated sample).

| No. | temp. [° C.] | residence time [sec] | water | conv. [%] | sel. 10-ODA [%] | sel. dehydration [%] |
|---|---|---|---|---|---|---|
| 1 | 500 | 2.2 | no | 25.6 | 18.7 | 10.3 |
| 2 | 500 | 2.1 | yes | 21.4 | 17.6 | 8.1 |
| 3 | 550 | 2.0 | no | 37.6 | 26.8 | 10.5 |
| 4 | 550 | 1.5 | no | 39.9 | 26.8 | 9.6 |
| 5 | 550 | 1.9 | yes | 39.2 | 29.8 | 11.6 |
| 6 | 550 | 1.3 | yes | 41.0 | 29.1 | 11.0 |
| 7 | 600 | 2.0 | no | 94.2 | 51.7 | 10.5 |
| 8 | 600 | 1.3 | yes | 99.5 | 74.2 | 6.5 | b. Pyrolysis of 10-hydroxyoctadec-12-enoic acid (10-hydroxy-12-octadecenoic acid)

As the use of 10-hydroxy-12-octadecenoic acid methyl ester as reactant would mean one more step in the overall scheme from linoleic acid to sebacic acid the successful microreactor setup was also tested using the free acid 10-hydroxy-12-octadecenoic acid (as 10 wt % solution in THF). In comparison to the pyrolysis of 10-hydroxy-12-octadecenoic acid methyl ester, full conversion of 10-hydroxy-12-octadecenoic acid is already obtained at lower temperatures (575° C., entry 5 in Table 3). As in the case of 10-hydroxy-12-octadecenoic acid methyl ester, the residence time does not influence the reaction to a large extent. Nevertheless, the selectivity towards 10-oxo-decanoic acid is significantly lower (48 vs. 74%, compare entry 8 in Table 2). More dehydration as side reaction is observed, which could be due to the poor vaporization behaviour of the free fatty acid compared to its methyl ester.

TABLE 3

Results of 10-hydroxy-12-octadecenoic acid pyrolysis in microreactor (analyzed by GC of silylated sample).

| No. | temp. [° C.] | residence time [sec] | conv. [%] | sel. 10-ODA [%] | sel. dehydration [%] |
|---|---|---|---|---|---|
| 1 | 500 | 2.0 | 27.2 | 17.0 | 8.5 |
| 2 | 525 | 1.9 | 42.3 | 21.3 | 18.7 |
| 3 | 550 | 1.9 | 72.2 | 32.3 | 35.1 |
| 4 | 550 | 1.4 | 73.0 | 33.2 | 32.8 |
| 5 | 575 | 1.9 | 99.8 | 48.3 | 38.1 |

Example 5

Oxidation of 10-Oxo-Decanoic Acid to Sebacic Acid

The oxidation of 10-oxo-decanoic acid to sebacic acid can be performed as described by H.-J. Arpe (Industrial Organic Chemistry, Wiley-VCH, 2007, pp. 149): The aldehyde is oxidized with mild oxidizing agents, as e.g. air or pure oxygen in liquid phase at up to 100° C. and up to 7 bar, either uncatalyzed or homogenously catalyzed by redox active metals, as e.g. Cu, Fe, Co, Mn.

The invention claimed is:

1. A process for preparing sebacic acid comprising
in a first step reacting (i) linoleic acid with water catalyzed by an oleate hydratase to form 10-hydroxy-12-octadecenoic acid,
in a second step (ii) pyrolysing the 10-hydroxy-12-octadecenoic acid to 1-octene and 10-oxo-decanoic acid, and
in a third step(iii) oxidizing the 10-oxo-decanoic acid to sebacic acid, wherein the oleate hydratase is a polypeptide having the amino acid sequence depicted in SEQ ID NO:2 or an amino acid sequence which is at least 95% identical to the amino acid sequence depicted in SEQ ID NO:2.

2. The process according to claim 1, wherein the oleate hydratase is a polypeptide having SEQ ID NO:2.

3. The process according to claim 1, wherein after step (i) the 10-hydroxy-12-octadecenoic acid is esterified to a 10-hydroxy-12-octadecenoic acid ester and subsequently the 10-hydroxy-12-octadecenoic acid ester is pyrolysed in step (ii).

4. The process according to claim 3, wherein the 10-hydroxy-12-octadecenoic acid ester is a methyl ester.

5. The process according to claim 1, wherein the pyrolysis in step (ii) is performed at a temperature between 400 and 800° C.

6. The process according to claim 1, wherein the pyrolysis is carried out in a microstructured apparatus.

7. The process according to claim 1, wherein the pyrolysis in step (ii) is performed in tetrahydrofuran as a solvent.

8. The process according to claim 1, wherein the oxidation in step (iii) is performed using air.

9. The process according to claim 1, wherein the oxidation step (iii) is catalyzed by a redox active metal.

10. The process according to claim 1, wherein the pyrolysis in step (ii) is performed at a temperature between 500 and 600° C.

11. The process according to claim 1, wherein the oleate hydratase has the Enzyme Commission number EC 4.2.1.53.

12. The process according to claim 1, wherein the oleate hydratase has at least 97% identity to SEQ ID NO:2.

* * * * *

SEQUENCE LISTING

<160> NUMBER OF SEQ ID NOS: 2

<210> SEQ ID NO 1
<211> LENGTH: 1941
<212> TYPE: DNA
<213> ORGANISM: Elizabethkingia meningoseptica
<220> FEATURE:
<221> NAME/KEY: CDS

<222> LOCATION: (1)..(1941)

<400> SEQUENCE: 1

| | | | | | | | | | | | | | | | | |
|---|---|---|---|---|---|---|---|---|---|---|---|---|---|---|---|---|
| atg | aat | ccg | att | acc | agc | aaa | ttt | gat | aaa | gtg | ctg | aat | gcc | agc | agc | 48 |
| Met | Asn | Pro | Ile | Thr | Ser | Lys | Phe | Asp | Lys | Val | Leu | Asn | Ala | Ser | Ser | |
| 1 | | | | 5 | | | | | 10 | | | | | 15 | | |
| gaa | tat | ggt | cat | gtt | aat | cat | gaa | ccg | gat | agc | agc | aaa | gaa | cag | cag | 96 |
| Glu | Tyr | Gly | His | Val | Asn | His | Glu | Pro | Asp | Ser | Ser | Lys | Glu | Gln | Gln | |
| | | | 20 | | | | | 25 | | | | | 30 | | | |
| cgt | aat | aca | ccg | cag | aaa | agc | atg | ccg | ttt | agc | gat | cag | att | ggt | aat | 144 |
| Arg | Asn | Thr | Pro | Gln | Lys | Ser | Met | Pro | Phe | Ser | Asp | Gln | Ile | Gly | Asn | |
| | | 35 | | | | | 40 | | | | | 45 | | | | |
| tat | cag | cgc | aat | aaa | ggt | att | ccg | gtg | cag | agc | tat | gat | aat | agc | aaa | 192 |
| Tyr | Gln | Arg | Asn | Lys | Gly | Ile | Pro | Val | Gln | Ser | Tyr | Asp | Asn | Ser | Lys | |
| | 50 | | | | | 55 | | | | | 60 | | | | | |
| att | tat | att | att | ggc | agc | ggc | att | gca | ggt | atg | agc | gca | gca | tat | tat | 240 |
| Ile | Tyr | Ile | Ile | Gly | Ser | Gly | Ile | Ala | Gly | Met | Ser | Ala | Ala | Tyr | Tyr | |
| 65 | | | | | 70 | | | | | 75 | | | | | 80 | |
| ttt | att | cgt | gat | ggc | cat | gtt | ccg | gca | aaa | aat | att | acc | ttt | ctg | gaa | 288 |
| Phe | Ile | Arg | Asp | Gly | His | Val | Pro | Ala | Lys | Asn | Ile | Thr | Phe | Leu | Glu | |
| | | | | 85 | | | | | 90 | | | | | 95 | | |
| cag | ctg | cat | att | gat | ggt | ggt | agc | ctg | gat | ggt | gca | ggt | aat | ccg | acc | 336 |
| Gln | Leu | His | Ile | Asp | Gly | Gly | Ser | Leu | Asp | Gly | Ala | Gly | Asn | Pro | Thr | |
| | | | 100 | | | | | 105 | | | | | 110 | | | |
| gat | ggt | tat | att | att | cgt | ggt | ggt | cgt | gaa | atg | gat | atg | acc | tat | gaa | 384 |
| Asp | Gly | Tyr | Ile | Ile | Arg | Gly | Gly | Arg | Glu | Met | Asp | Met | Thr | Tyr | Glu | |
| | | 115 | | | | | 120 | | | | | 125 | | | | |
| aat | ctg | tgg | gac | atg | ttt | cag | gat | att | ccg | gca | ctg | gaa | atg | cct | gca | 432 |
| Asn | Leu | Trp | Asp | Met | Phe | Gln | Asp | Ile | Pro | Ala | Leu | Glu | Met | Pro | Ala | |
| | 130 | | | | | 135 | | | | | 140 | | | | | |
| ccg | tat | agc | gtt | ctg | gat | gaa | tat | cgt | ctg | att | aat | gat | aat | gat | agc | 480 |
| Pro | Tyr | Ser | Val | Leu | Asp | Glu | Tyr | Arg | Leu | Ile | Asn | Asp | Asn | Asp | Ser | |
| 145 | | | | | 150 | | | | | 155 | | | | | 160 | |
| aat | tat | agc | aaa | gca | cgc | ctg | att | aat | aac | aaa | ggc | gaa | att | aaa | gat | 528 |
| Asn | Tyr | Ser | Lys | Ala | Arg | Leu | Ile | Asn | Asn | Lys | Gly | Glu | Ile | Lys | Asp | |
| | | | | 165 | | | | | 170 | | | | | 175 | | |
| ttt | agc | aaa | ttt | ggc | ctg | aat | aaa | atg | gat | cag | ctg | gca | att | att | cgc | 576 |
| Phe | Ser | Lys | Phe | Gly | Leu | Asn | Lys | Met | Asp | Gln | Leu | Ala | Ile | Ile | Arg | |
| | | | 180 | | | | | 185 | | | | | 190 | | | |
| ctg | ctg | ctg | aaa | aat | aaa | gaa | gaa | ctg | gac | gat | ctg | acc | att | gaa | gat | 624 |
| Leu | Leu | Leu | Lys | Asn | Lys | Glu | Glu | Leu | Asp | Asp | Leu | Thr | Ile | Glu | Asp | |
| | | 195 | | | | | 200 | | | | | 205 | | | | |
| tat | ttt | agc | gaa | agt | ttt | ctg | aaa | agc | aat | ttt | tgg | acc | ttt | tgg | cgt | 672 |
| Tyr | Phe | Ser | Glu | Ser | Phe | Leu | Lys | Ser | Asn | Phe | Trp | Thr | Phe | Trp | Arg | |
| | 210 | | | | | 215 | | | | | 220 | | | | | |
| acc | atg | ttt | gcc | ttt | gaa | aat | tgg | cat | agc | ctg | ctg | gaa | ctg | aaa | ctg | 720 |
| Thr | Met | Phe | Ala | Phe | Glu | Asn | Trp | His | Ser | Leu | Leu | Glu | Leu | Lys | Leu | |
| 225 | | | | | 230 | | | | | 235 | | | | | 240 | |
| tat | atg | cat | cgt | ttt | ctg | cat | gcc | att | gat | ggt | ctg | aat | gat | ctg | agc | 768 |
| Tyr | Met | His | Arg | Phe | Leu | His | Ala | Ile | Asp | Gly | Leu | Asn | Asp | Leu | Ser | |
| | | | | 245 | | | | | 250 | | | | | 255 | | |
| agc | ctg | gtt | ttt | ccg | aaa | tac | aat | cag | tat | gat | acc | ttt | gtt | aca | ccg | 816 |
| Ser | Leu | Val | Phe | Pro | Lys | Tyr | Asn | Gln | Tyr | Asp | Thr | Phe | Val | Thr | Pro | |
| | | | 260 | | | | | 265 | | | | | 270 | | | |
| ctg | cgt | aaa | ttt | ctg | cag | gaa | aaa | ggc | gtt | aat | att | cat | ctg | aat | acc | 864 |
| Leu | Arg | Lys | Phe | Leu | Gln | Glu | Lys | Gly | Val | Asn | Ile | His | Leu | Asn | Thr | |
| | | 275 | | | | | 280 | | | | | 285 | | | | |
| ctg | gtg | aaa | gat | ctg | gat | att | cat | att | aat | acc | gaa | ggc | aaa | gtg | gtg | 912 |
| Leu | Val | Lys | Asp | Leu | Asp | Ile | His | Ile | Asn | Thr | Glu | Gly | Lys | Val | Val | |
| | | 290 | | | | | 295 | | | | | 300 | | | | |

```
gaa ggc att att acc gaa cag gat ggt aaa gaa gtg aaa att ccg gtt    960
Glu Gly Ile Ile Thr Glu Gln Asp Gly Lys Glu Val Lys Ile Pro Val
305                 310                 315                 320 ggc aaa aat gat tat gtg att gtt acc acc ggc agc atg acc gaa gat   1008
Gly Lys Asn Asp Tyr Val Ile Val Thr Thr Gly Ser Met Thr Glu Asp
                325                 330                 335 acc ttt tat ggc aat aat aaa acc gca ccg att att ggc att gat aat   1056
Thr Phe Tyr Gly Asn Asn Lys Thr Ala Pro Ile Ile Gly Ile Asp Asn
            340                 345                 350 agc acc agc ggt cag agc gca ggt tgg aaa ctg tgg aaa aat ctg gca   1104
Ser Thr Ser Gly Gln Ser Ala Gly Trp Lys Leu Trp Lys Asn Leu Ala
        355                 360                 365 gca aaa agc gaa att ttt ggc aaa ccg gaa aaa ttt tgc agc aat att   1152
Ala Lys Ser Glu Ile Phe Gly Lys Pro Glu Lys Phe Cys Ser Asn Ile
    370                 375                 380 gaa aaa agc gca tgg gaa agc gca acc ctg acc tgt aaa ccg agc gca   1200
Glu Lys Ser Ala Trp Glu Ser Ala Thr Leu Thr Cys Lys Pro Ser Ala
385                 390                 395                 400 ctg att gat aaa ctg aaa gaa tat agc gtg aat gat ccg tat agc ggt   1248
Leu Ile Asp Lys Leu Lys Glu Tyr Ser Val Asn Asp Pro Tyr Ser Gly
                405                 410                 415 aaa acc gtt acc ggt ggt att att acc att acc gat agc aat tgg ctg   1296
Lys Thr Val Thr Gly Gly Ile Ile Thr Ile Thr Asp Ser Asn Trp Leu
                420                 425                 430 atg agc ttt acc tgt aat cgt cag ccg cat ttt ccg gaa cag ccg gat   1344
Met Ser Phe Thr Cys Asn Arg Gln Pro His Phe Pro Glu Gln Pro Asp
        435                 440                 445 gat gtt ctg gtt ctg tgg gtt tat gca ctg ttt atg gat aaa gaa ggc   1392
Asp Val Leu Val Leu Trp Val Tyr Ala Leu Phe Met Asp Lys Glu Gly
    450                 455                 460 aat tat att aaa aaa acc atg ctg gaa tgc acc ggt gat gaa att ctg   1440
Asn Tyr Ile Lys Lys Thr Met Leu Glu Cys Thr Gly Asp Glu Ile Leu
465                 470                 475                 480 gca gaa ctg tgt tat cat ctg ggt att gaa gat cag ctg gaa aat gtg   1488
Ala Glu Leu Cys Tyr His Leu Gly Ile Glu Asp Gln Leu Glu Asn Val
                485                 490                 495 cag aaa aat acc att gtt cgc acc gca ttt atg ccg tat att acc agc   1536
Gln Lys Asn Thr Ile Val Arg Thr Ala Phe Met Pro Tyr Ile Thr Ser
                500                 505                 510 atg ttt atg cct cgt gca aaa ggt gat cgt ccg cgt gtt gtt ccg gaa   1584
Met Phe Met Pro Arg Ala Lys Gly Asp Arg Pro Arg Val Val Pro Glu
        515                 520                 525 ggt tgt aaa aat ctg ggt ctg gtt ggt cag ttt gtg gaa acc aat aat   1632
Gly Cys Lys Asn Leu Gly Leu Val Gly Gln Phe Val Glu Thr Asn Asn
    530                 535                 540 gat gtg gtg ttt acc atg gaa agc agc gtt cgt acc gca cgt att gcc   1680
Asp Val Val Phe Thr Met Glu Ser Ser Val Arg Thr Ala Arg Ile Ala
545                 550                 555                 560 gtt tat aaa ctg ctg aat ctg aat aaa cag gtg ccg gat att aat ccg   1728
Val Tyr Lys Leu Leu Asn Leu Asn Lys Gln Val Pro Asp Ile Asn Pro
                565                 570                 575 ctg cag tat gat att cgt cat ctg ctg aaa gca gcc aaa acc ctg aat   1776
Leu Gln Tyr Asp Ile Arg His Leu Leu Lys Ala Ala Lys Thr Leu Asn
                580                 585                 590 gat gat aaa ccg ttt gtt ggt gaa ggt ctg ctg cgc aaa gtt ctg aaa   1824
Asp Asp Lys Pro Phe Val Gly Glu Gly Leu Leu Arg Lys Val Leu Lys
                595                 600                 605 ggc acc tat ttt gaa cat gtt ctg cca gca ggc gca gcc gaa gaa gaa   1872
Gly Thr Tyr Phe Glu His Val Leu Pro Ala Gly Ala Ala Glu Glu Glu
```

```
                610                 615                 620
gaa cac gaa agt ttt att gcc gaa cat gtg aat aaa ttt cgc gaa tgg    1920
Glu His Glu Ser Phe Ile Ala Glu His Val Asn Lys Phe Arg Glu Trp
625                 630                 635                 640 gtg aaa ggt att cgc ggt taa                                        1941
Val Lys Gly Ile Arg Gly
                645

<210> SEQ ID NO 2
<211> LENGTH: 646
<212> TYPE: PRT
<213> ORGANISM: Elizabethkingia meningoseptica

<400> SEQUENCE: 2

Met Asn Pro Ile Thr Ser Lys Phe Asp Lys Val Leu Asn Ala Ser Ser
1               5                   10                  15

Glu Tyr Gly His Val Asn His Glu Pro Asp Ser Ser Lys Glu Gln Gln
            20                  25                  30

Arg Asn Thr Pro Gln Lys Ser Met Pro Phe Ser Asp Gln Ile Gly Asn
        35                  40                  45

Tyr Gln Arg Asn Lys Gly Ile Pro Val Gln Ser Tyr Asp Asn Ser Lys
    50                  55                  60

Ile Tyr Ile Ile Gly Ser Gly Ile Ala Gly Met Ser Ala Ala Tyr Tyr
65                  70                  75                  80

Phe Ile Arg Asp Gly His Val Pro Ala Lys Asn Ile Thr Phe Leu Glu
                85                  90                  95

Gln Leu His Ile Asp Gly Gly Ser Leu Asp Gly Ala Gly Asn Pro Thr
            100                 105                 110

Asp Gly Tyr Ile Ile Arg Gly Gly Arg Glu Met Asp Met Thr Tyr Glu
        115                 120                 125

Asn Leu Trp Asp Met Phe Gln Asp Ile Pro Ala Leu Glu Met Pro Ala
    130                 135                 140

Pro Tyr Ser Val Leu Asp Glu Tyr Arg Leu Ile Asn Asp Asn Asp Ser
145                 150                 155                 160

Asn Tyr Ser Lys Ala Arg Leu Ile Asn Asn Lys Gly Glu Ile Lys Asp
                165                 170                 175

Phe Ser Lys Phe Gly Leu Asn Lys Met Asp Gln Leu Ala Ile Ile Arg
            180                 185                 190

Leu Leu Leu Lys Asn Lys Glu Glu Leu Asp Asp Leu Thr Ile Glu Asp
        195                 200                 205

Tyr Phe Ser Glu Ser Phe Leu Lys Ser Asn Phe Trp Thr Phe Trp Arg
    210                 215                 220

Thr Met Phe Ala Phe Glu Asn Trp His Ser Leu Leu Glu Leu Lys Leu
225                 230                 235                 240

Tyr Met His Arg Phe Leu His Ala Ile Asp Gly Leu Asn Asp Leu Ser
                245                 250                 255

Ser Leu Val Phe Pro Lys Tyr Asn Gln Tyr Asp Thr Phe Val Thr Pro
            260                 265                 270

Leu Arg Lys Phe Leu Gln Glu Lys Gly Val Asn Ile His Leu Asn Thr
        275                 280                 285

Leu Val Lys Asp Leu Asp Ile His Ile Asn Thr Glu Gly Lys Val Val
    290                 295                 300

Glu Gly Ile Ile Thr Glu Gln Asp Gly Lys Glu Val Lys Ile Pro Val
305                 310                 315                 320

Gly Lys Asn Asp Tyr Val Ile Val Thr Thr Gly Ser Met Thr Glu Asp
```

-continued

```
                        325                 330                 335
Thr Phe Tyr Gly Asn Asn Lys Thr Ala Pro Ile Ile Gly Ile Asp Asn
                    340                 345                 350
Ser Thr Ser Gly Gln Ser Ala Gly Trp Lys Leu Trp Lys Asn Leu Ala
                355                 360                 365
Ala Lys Ser Glu Ile Phe Gly Lys Pro Glu Lys Phe Cys Ser Asn Ile
            370                 375                 380
Glu Lys Ser Ala Trp Glu Ser Ala Thr Leu Thr Cys Lys Pro Ser Ala
385                 390                 395                 400
Leu Ile Asp Lys Leu Lys Glu Tyr Ser Val Asn Asp Pro Tyr Ser Gly
                405                 410                 415
Lys Thr Val Thr Gly Gly Ile Ile Thr Ile Thr Asp Ser Asn Trp Leu
                420                 425                 430
Met Ser Phe Thr Cys Asn Arg Gln Pro His Phe Pro Glu Gln Pro Asp
                435                 440                 445
Asp Val Leu Val Leu Trp Val Tyr Ala Leu Phe Met Asp Lys Glu Gly
450                 455                 460
Asn Tyr Ile Lys Lys Thr Met Leu Glu Cys Thr Gly Asp Glu Ile Leu
465                 470                 475                 480
Ala Glu Leu Cys Tyr His Leu Gly Ile Glu Asp Gln Leu Glu Asn Val
                485                 490                 495
Gln Lys Asn Thr Ile Val Arg Thr Ala Phe Met Pro Tyr Ile Thr Ser
                500                 505                 510
Met Phe Met Pro Arg Ala Lys Gly Asp Arg Pro Arg Val Val Pro Glu
                515                 520                 525
Gly Cys Lys Asn Leu Gly Leu Val Gly Gln Phe Val Glu Thr Asn Asn
                530                 535                 540
Asp Val Val Phe Thr Met Glu Ser Ser Val Arg Thr Ala Arg Ile Ala
545                 550                 555                 560
Val Tyr Lys Leu Leu Asn Leu Asn Lys Gln Val Pro Asp Ile Asn Pro
                565                 570                 575
Leu Gln Tyr Asp Ile Arg His Leu Leu Lys Ala Ala Lys Thr Leu Asn
                580                 585                 590
Asp Asp Lys Pro Phe Val Gly Glu Gly Leu Leu Arg Lys Val Leu Lys
            595                 600                 605
Gly Thr Tyr Phe Glu His Val Leu Pro Ala Gly Ala Ala Glu Glu Glu
            610                 615                 620
Glu His Glu Ser Phe Ile Ala Glu His Val Asn Lys Phe Arg Glu Trp
625                 630                 635                 640
Val Lys Gly Ile Arg Gly
                645
```